(12) United States Patent
Hwang et al.

(10) Patent No.: US 7,518,734 B2
(45) Date of Patent: Apr. 14, 2009

(54) APPARATUS AND METHOD OF MEASURING THICKNESS OF LINGUAL FUR AND ACQUIRING VERTICAL SECTION IMAGE THEREOF

(75) Inventors: In-duk Hwang, Suwon-si (KR); Sang-hoon Shin, Seongnam-si (KR); Ki-wang Kim, Donbong-gu (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 337 days.

(21) Appl. No.: 11/272,141

(22) Filed: Nov. 14, 2005

(65) Prior Publication Data
US 2006/0119860 A1 Jun. 8, 2006

(30) Foreign Application Priority Data
Nov. 13, 2004 (KR) .................... 10-2004-0092808

(51) Int. Cl.
*G01B 11/02* (2006.01)

(52) U.S. Cl. .................................. 356/511; 356/497
(58) Field of Classification Search ................ 356/479, 356/497, 511
See application file for complete search history.

(56) References Cited

U.S. PATENT DOCUMENTS

| 5,710,630 | A * | 1/1998 | Essenpreis et al. | 356/479 |
| 5,716,324 | A * | 2/1998 | Toida | 600/160 |
| 5,810,719 | A * | 9/1998 | Toida | 600/160 |
| 6,161,031 | A * | 12/2000 | Hochman et al. | 600/407 |
| 6,725,073 | B1 * | 4/2004 | Motamedi et al. | 600/316 |
| 2003/0236458 | A1 * | 12/2003 | Hochman | 600/431 |
| 2006/0247502 | A1 * | 11/2006 | Chen | 600/300 |

* cited by examiner

*Primary Examiner*—Patrick J Connolly
(74) *Attorney, Agent, or Firm*—Staas & Halsey LLP

(57) ABSTRACT

A method of acquiring a vertical section image of lingual fur, and an apparatus to perform the method, the method including generating interfering light from irradiated light and light reflected from a tongue tissue, and generating a partial image corresponding to a relative intensity of the generated interfering light.

31 Claims, 5 Drawing Sheets

APPARATUS AND METHOD OF MEASURING THICKNESS OF LINGUAL FUR AND ACQUIRING VERTICAL SECTION IMAGE THEREOF

CROSS-REFERENCE TO RELATED APPLICATIONS

This application claims the benefit of Korean Patent Application No. 10-2004-0092808, filed on Nov. 13, 2004, in the Korean Intellectual Property Office, the disclosure of which is incorporated herein by reference.

BACKGROUND OF THE INVENTION

1. Field of the Invention

The present invention relates to acquisition of a vertical section image, and, more particularly, to a method of measuring the thickness of lingual fur and acquiring a vertical section image thereof using interfering light, and an apparatus to perform the method.

2. Description of the Related Art

The tongue indicates health conditions of persons. For example, the tip of the tongue, that is, the lingual apex, indicates cardiopulmonary conditions, and the root of the tongue, that is, the lingual radix, indicates renal conditions.

In addition to the tongue, lingual fur can be used as an indicator of health conditions. The lingual fur refers to a moss-like growth generated on the surface of the tongue. The lingual fur includes epithelium tissues, lymph tissues, food remnants, etc., and may be in a variety of colors.

A health condition of a person can be indicated by the shape in which the lingual fur is distributed on the tongue, the color of the lingual fur, and the thickness of the lingual fur.

For example, when a person has peracidity due to overeating, little lingual fur exists, or a very thin white lingual fur exists, on the tongue. Conversely, when a person has typhoid, thick white or brown lingual fur exists at the center of the tongue. Such thick lingual fur may appear due to excessive drinking, gastritis, attack of fever, etc., and lasts for a long time.

FIG. 1 is a block diagram illustrating a conventional lingual-fur observation apparatus. In the figure, a communication terminal 110 photographs a lingual fur and supplies color information regarding the photographed lingual fur to an administration server 120.

The administration server 120 supplies the color information to a diagnosis and prescription server 130 and/or an Oriental medicine provider server 140.

The diagnosis and prescription server 130 is a server storing prescriptions corresponding to colors of lingual fur in a database. The diagnosis and prescription server 130 searches the database for a prescription corresponding to the supplied color information, and supplies the results, i.e., the corresponding prescription, to the administration server 120.

When no prescription is found in the database, the diagnosis and prescription server 130 notifies the Oriental medicine provider server 140 of "no prescription". Then, the Oriental medicine provider server 140 receives a prescription directly from a doctor of Oriental medicine, and supplies the received prescription to the administration server 120.

The administration server 120 is supplied with the prescription from the diagnosis and prescription server 130, or the Oriental medicine provider server 140, and notifies the communication terminal 110 of the prescription. The user can obtain information regarding his/her health condition with the communication terminal 110.

However, the conventional lingual fur observation apparatus has a problem in that only the color of lingual fur can be observed, but the thickness of the lingual fur cannot be measured, thereby causing a problem in that a correct prescription corresponding to the thickness of the lingual fur cannot be provided. In addition, the conventional lingual fur observation apparatus can only supply an image of lingual fur seen from a top view, and cannot supply a vertical section image of the lingual fur.

SUMMARY OF THE INVENTION

The present invention provides a method of measuring the thickness of lingual fur and acquiring a vertical section image thereof, and an apparatus to perform the method, which can more precisely examine lingual fur by measuring the thickness of the lingual fur and acquiring a vertical section image thereof.

Additional aspects and/or advantages of the invention will be set forth in part in the description which follows and, in part, will be apparent from the description, or may be learned by practice of the invention.

According to an aspect of the present invention, there is provided an apparatus to acquire a vertical section image of lingual fur, the apparatus comprising: a light irradiating unit having a light source to irradiate light, the light source being movable; an optical probe to receive the light irradiated from the light source and deliver the light to a tongue tissue; an optical device to generate interfering light from the light irradiated from the light irradiating unit and the light reflected from the tongue tissue; and an image generating unit to generate a partial image corresponding to a relative intensity of the generated interfering light.

According to another aspect of the present invention, there is provided an apparatus to acquire a vertical section image of lingual fur, the apparatus comprising: a light reflecting unit to receive light irradiated from a first predetermined light source and reflect the light; an optical probe to receive light irradiated from a second predetermined light source and deliver the light to a tongue tissue; an optical device to generate interfering light from the light reflected by the light reflecting unit and the light reflected from the tongue tissue; and an image generating unit to generate a partial image corresponding to a relative intensity of the generated interfering light.

The first predetermined light source applying light to the light reflecting unit and the second predetermined light source applying light to the optical probe may comprise a single light source, wherein the light reflecting unit reflects a first part of the light irradiated by the single light source, wherein the optical probe irradiates a second part of the light irradiated by the single light source to the tongue tissue, and wherein the optical device divides the light irradiated from the single light source into light irradiated to the light reflecting unit and light irradiated to the optical probe, and generates the interfering light from the light reflected by the light reflecting unit and the light reflected from the tongue tissue.

The light reflecting unit may comprise a reflecting mirror to reflect the received light, and a driving motor to change a distance that the light irradiated to the reflecting mirror travels until reaching the reflecting mirror by moving the reflecting mirror.

According to still another aspect of the present invention, there is provided a method of acquiring a vertical section image of lingual fur, the method comprising: generating interfering light from irradiated light and light reflected from a tongue tissue; and generating a partial image corresponding to a relative intensity of the generated interfering light.

According to yet another aspect of the present invention, there is provided a method of acquiring a vertical section image of lingual fur, the method comprising: dividing irradiated light into a first part and a second part; generating interfering light from reflected light of the first part of the light and reflected light from a tongue tissue generated by irradiating the second part of the light to the tongue tissue; and generating a partial image corresponding to a relative intensity of the generated interfering light.

The generation of the interfering light may include varying a distance that the first part of the light travels from a point at which the irradiated light is divided to a point at which the first part of the light is reflected, and wherein the generation of the partial image includes synthesizing a plurality of partial images corresponding to the varied distances that the first part of light travels, and generating the vertical section image.

The method may further comprise generating details of a prescription corresponding to the generated image.

The method may further comprise displaying the generated vertical section image.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE PREFERRED EMBODIMENTS

Figure 1:
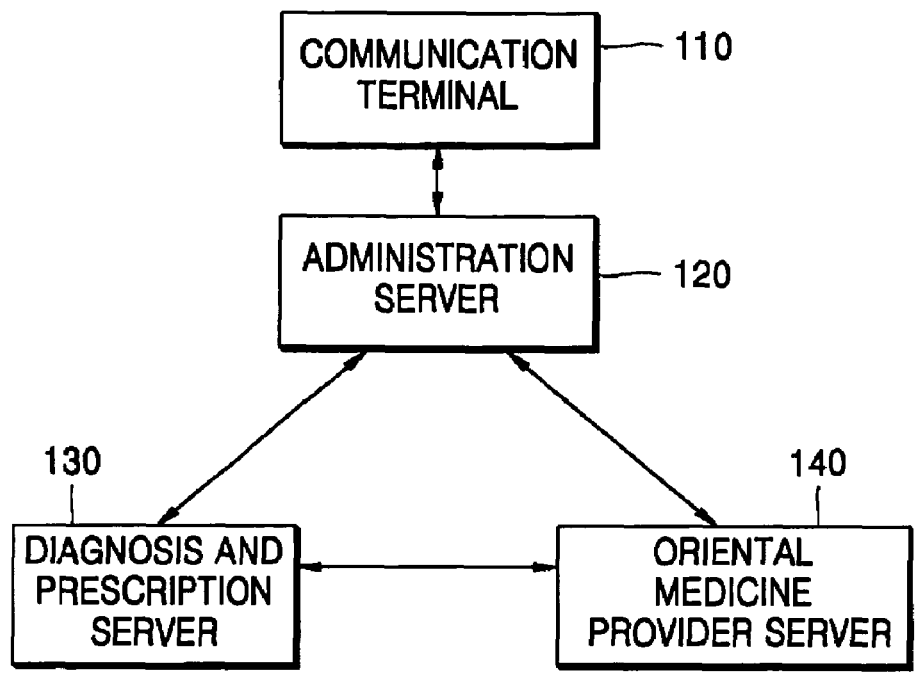
FIG. 1 is a block diagram illustrating a conventional lingual fur observation apparatus.

Reference will now be made in detail to the embodiments of the present invention, examples of which are illustrated in the accompanying drawings, wherein like reference numerals refer to the like elements throughout. The embodiments are described below to explain the present invention by referring to the figures. Functions in the present invention are taken into consideration in defining terms to be described later, therefore the terms may be changed depending upon intentions of users or administrators or customs. Therefore, the definitions should be made based on the entire description of the present invention.

Figure 2:
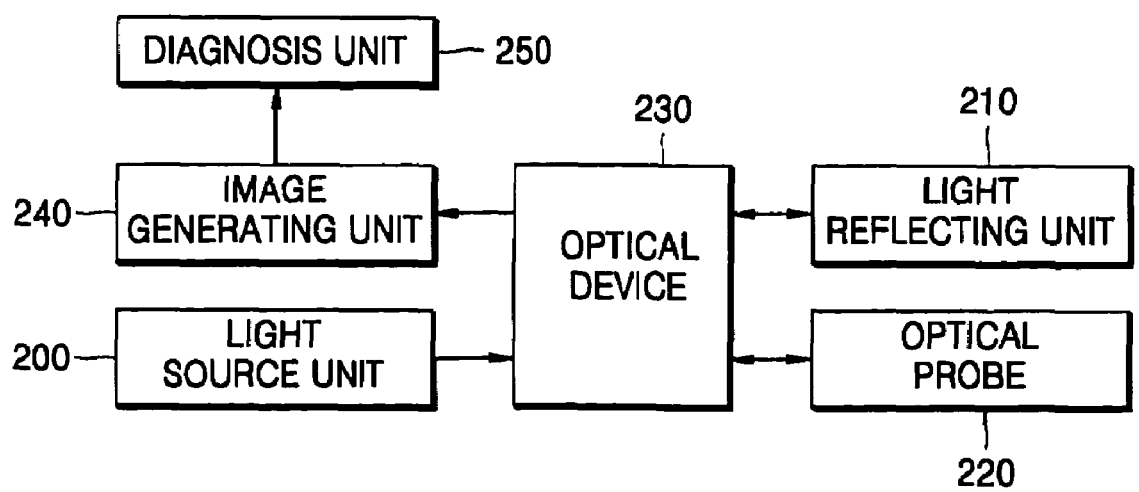
FIG. 2 is a block diagram illustrating an apparatus to measure the thickness of lingual fur and acquire a vertical section image thereof according to an embodiment of the present invention.

FIG. 2 is a block diagram illustrating an apparatus to measure the thickness of lingual fur, and to acquire a vertical section image thereof, according to an embodiment of the present invention (hereinafter referred to as "the present apparatus").

As shown in FIG. 2, the present apparatus includes a light source unit 200, a light reflecting unit 210, an optical probe 220, an optical device 230, an image generating unit 240, and a diagnosis unit 250. It is preferable, though not necessary, that the components are connected to one another through optical cables.

The light source unit 200 irradiates light, and can be embodied as an LED, LD, and the like. Preferably, though not necessarily, the light irradiated by the light source unit 200 has a wavelength ranging from approximately 700 nm to 1,300 nm, and a bandwidth of several tens of nm.

Figure 3:
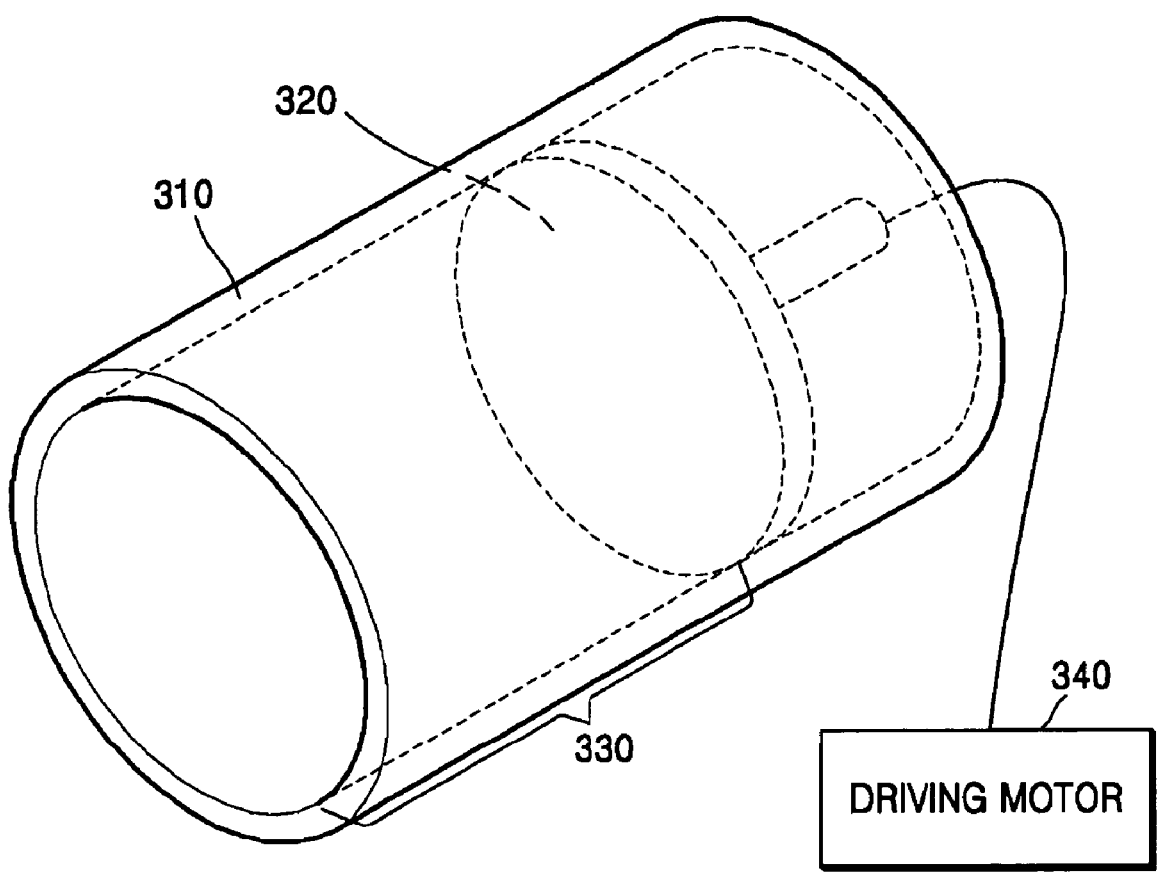
FIG. 3 is a view illustrating a structure of a light reflecting unit.

The light reflecting unit 210 reflects a first part of the light irradiated by the light source unit 200. The reflection is preferably, though not necessarily, total reflection, and hereinafter the light reflected by the light reflecting unit 210 is referred to as totally-reflected light. FIG. 3 is a view illustrating a structure of the light reflecting unit 210. Referring to FIG. 3, the light reflecting unit 210 may include a light passage 310, a reflecting mirror 320, and a driving motor 340. The light passage 310 serves as a path through which the light received by the light reflecting unit 210 travels, and includes a through-hole corresponding to the path. The reflecting mirror 320 reflects the received light. The driving motor 340 moves the reflecting mirror 320, and thus varies a light traveling distance 330, which is a distance which the light received by the reflecting mirror 320 travels until the light reaches the reflecting mirror 320. The reflecting mirror 320 may be moved in a state in which it is inserted into the through-hole of the light passage 310, or may be moved outside of the light passage 310. It is preferable, though not necessary, that a lens used to keep the light traveling in a constant direction toward the reflecting mirror 320 is provided at the inside of the light passage 310.

The optical probe 220 delivers a second part of the light irradiated by the light source unit 200 to a tongue tissue. Therefore, when fur exists on the tongue, the light delivered by the optical probe 220 is irradiated to both the lingual fur and the tongue tissue. A part of the light delivered by the optical probe 220 is absorbed by the lingual fur and the tongue tissue, and another part of the light is reflected thereby.

The optical probe 220 may further include an optical film (not shown). The second part of the light delivered by the optical probe 220 can be delivered through a predetermined optical cable. The optical film may be connected to one end of the optical cable, and comes in close contact with the lingual fur and the tongue tissue. The optical film serves to optically completely couple the optical cable and the lingual fur to each other. It is preferable, though not necessary, that a lens used to keep the light traveling in a constant direction toward the optical film is provided at the inside of the optical cable.

Figure 4:
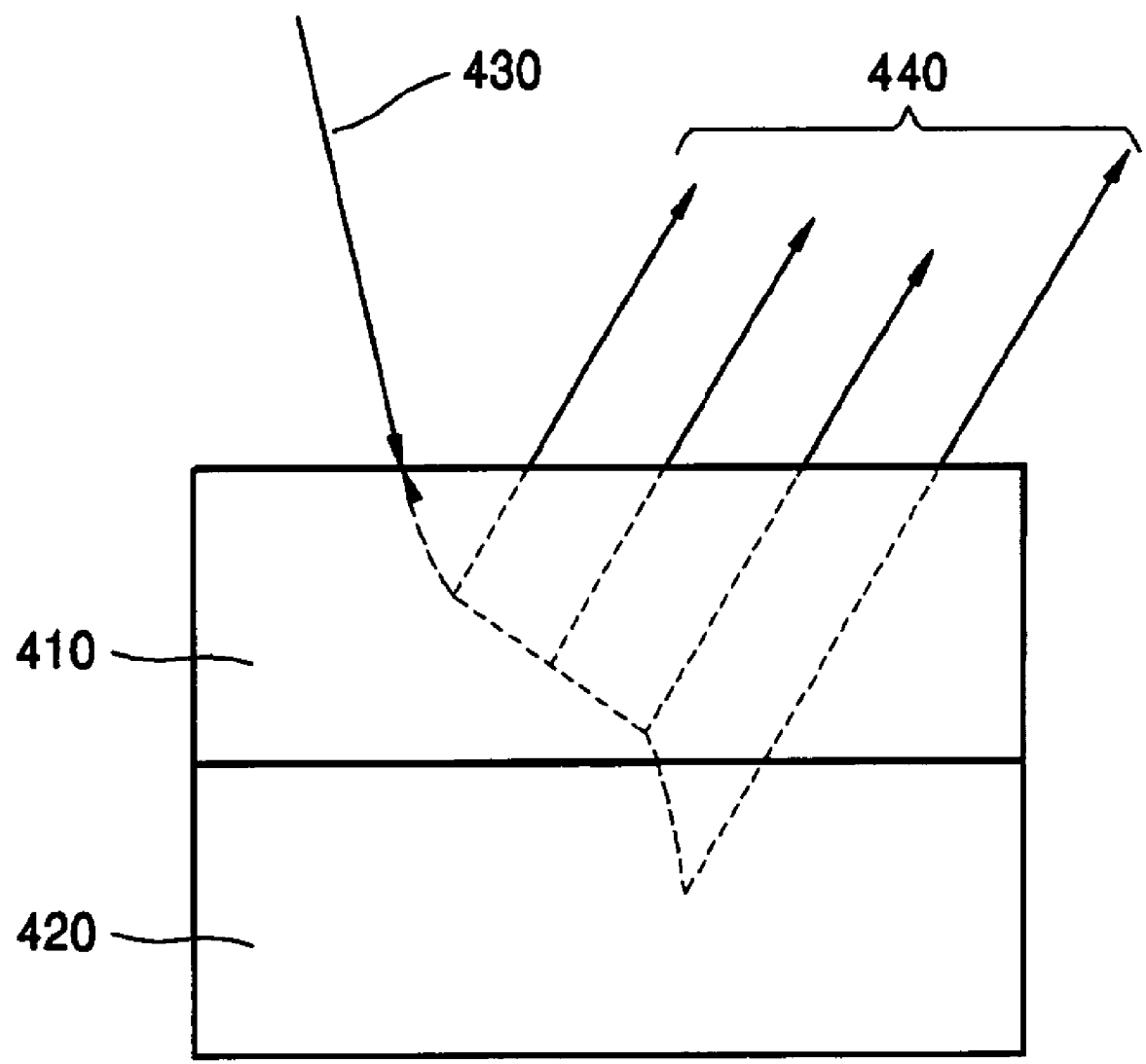
FIG. 4 is a view illustrating a state in which light is irradiated to, and reflected from, lingual fur and tongue tissue.

FIG. 4 is a view illustrating a state in which light is irradiated to, and reflected by, the lingual fur and the tongue tissue. In the figure, the light 430 irradiated through the optical cable is obliquely incident on the lingual fur 410, but this is intended only for easy illustration of the process. In fact, it is preferable, though not necessary, that the light 430 is vertically incident on the lingual fur 410. This is because the optical film comes in close contact with the lingual fur 410. The incident light 430 collides with fine particles (hereinafter, referred to as "target particles") constituting the lingual fur 410 and the tongue tissue 420 while passing through the lingual fur 410 and the tongue tissue 420, and a part of the incident light 430 is converted into part of reflected light 440 during the collision. Since the intensity of the incident light 430 decreases with the depth of its penetration, the intensity of the reflected light 440 generally becomes weaker as the depth of the target particles reflecting the light becomes greater.

It is preferable, though not necessary, that the optical film of the optical probe 220 is vertically and horizontally movable on the surface of the lingual fur.

The optical device 230 serves as a divider to divide the light from the light source unit 200 into the first part of the light supplied to the light reflecting unit 210, and the second part of the light irradiated to the optical probe 220. The division of the light is preferably, though not necessarily, performed so that the quantity of light supplied to the light reflecting unit 210 and the quantity of light irradiated to the optical probe 220 are approximately equal to each other.

The optical device 230 generates interfering light, obtained by making the light reflected by the light reflecting unit 210 and the light reflected from the tongue tissue 420 or the lingual fur 410 interfere with each other, and serves as a coupler. As a result, the optical device 230 simultaneously serves as a divider and a coupler.

The image generating unit 240 generates partial images corresponding to the relative intensities of the interfering light generated by the optical device 230. For example, by mapping a greater intensity to a brighter point, and mapping a smaller intensity to a darker point, the partial images can be generated. Preferably, though not necessarily, factors determining the intensity of the interfering light include the depth of a target particle's position, and the composition of the target particle.

The image generating unit 240 synthesizes a plurality of the partial images generated at intervals of the predetermined light traveling distance 330, and generates a vertical section image of the lingual fur. When the light traveling distance 330 is changed, the interfering light is generated at intervals of a predetermined time, and the interfering light reflected by a target particle having a small depth is first generated.

It is preferable, though not necessary, that the changed values of the light traveling distance 330 correspond to differences in depth of the target particles.

As a result, since the totally-reflected light and the interfering light are generated in the order of depths of the target particles, a vertical section image indicating a distribution of the target particles can be obtained by synthesizing the partial images corresponding to all the generated interfering parts of the light. Here, term "vertical" means "perpendicular to the surface of the lingual fur". The "vertical section image" refers to an image indicating the distributions of all the target particles existing vertically from one point on the surface of the lingual fur. Since the vertical section image of the lingual fur 410 and the vertical section image of the tongue tissue 420 are distinguishable, the vertical section image also indicates the thickness of the lingual fur 410.

If the optical film of the optical probe 220 is moved horizontally and vertically on the surface of the lingual fur, the vertical section images of multiple points on the surface of the lingual fur can be obtained.

As a result, the distribution image of the lingual fur 410 in a horizontal plane and the distribution image of the lingual fur 410 in a vertical plane can be obtained using the present apparatus. The terms "vertical" and "horizontal" are determined with respect to the surface of the lingual fur. The distribution image of the lingual fur in a vertical plane is a set of the vertical section images.

The diagnosis unit 250 is supplied with the vertical section image and/or the distribution image from the image generating unit 240, and generates prescription details corresponding to the supplied image. Accordingly, the present apparatus can supply a prescription to a user in real time.

Figure 5:
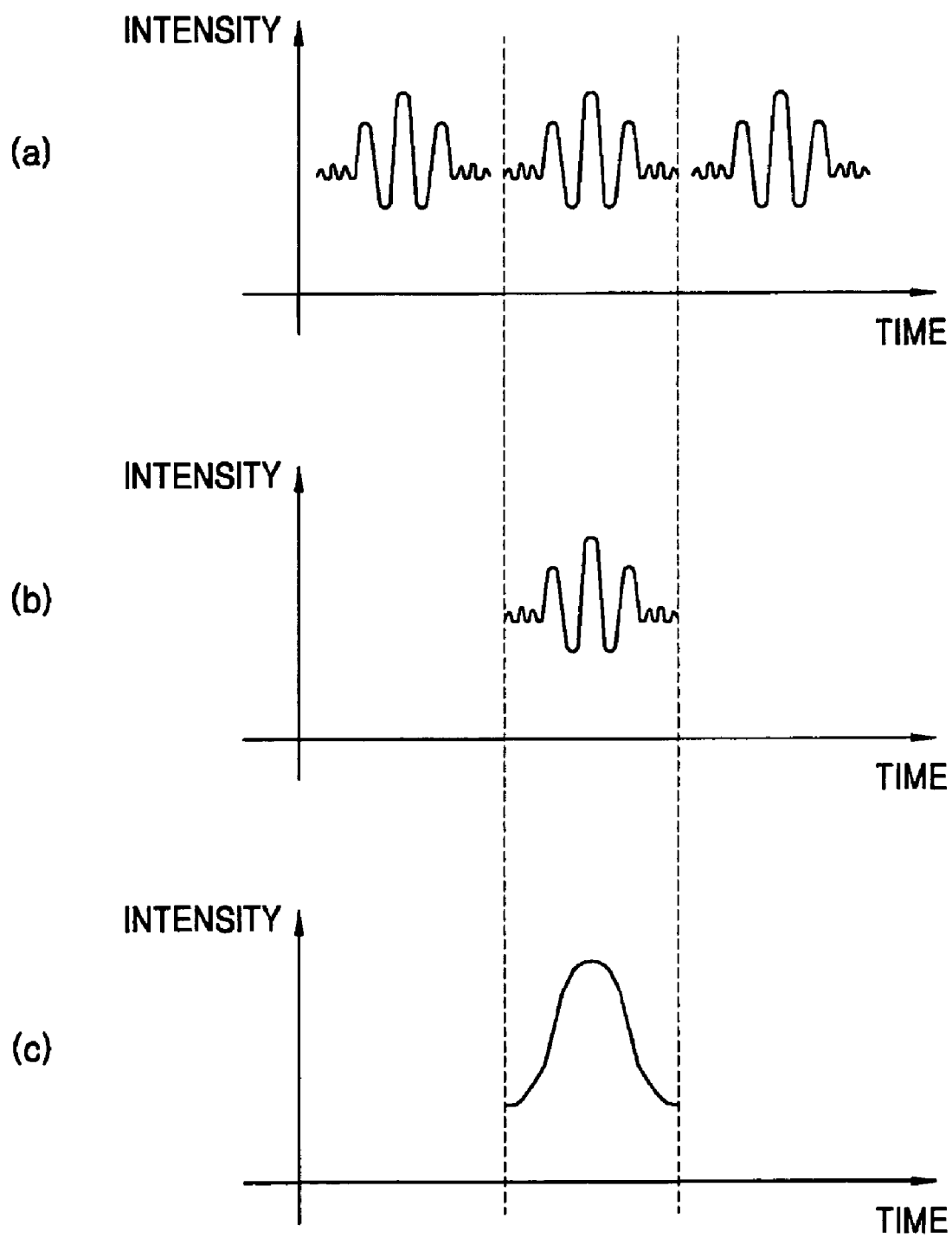
FIG. 5 part (a) is a graph expressing the intensity of light reflected from the tongue tissue with respect to a time axis, FIG. 5 part (b) is a graph expressing the intensity of light reflected by a light reflecting unit with respect to a time axis, and FIG. 5 part (c) is a graph expressing the intensity of interfering light with respect to a time axis.

FIG. 5 part (a) is a graph expressing the intensity of light reflected from the tongue tissue with respect to a time axis, FIG. 5 part (b) is a graph expressing the intensity of light reflected by the light reflecting unit 210 with respect to a time axis, and FIG. 5 part (c) is a graph expressing the intensity of interfering light with respect to a time axis.

Referring to FIG. 5 part (a), a plurality of reflected light is generated with time. The reflected light refers to the reflected light 440 shown in FIG. 4. Since the reflected light is generated for each target particle of the lingual fur 410 and the tongue tissue 420, the reflected light is continuously generated. Only three reflected parts of light 440 are shown in FIG. 5 part (a), for the purpose of convenient explanation.

Referring to FIG. 5 part (b), one totally-reflected light portion is observed. This is because the totally-reflected light is generated specifically to each light traveling distance 330. When the reflecting mirror 320 is moved, and the light traveling distance 330 is increased, the totally-reflected light detected by the optical device 230 is observed as light having a smaller intensity with a time delay. Since the reflected light 440 obtained by the optical probe 220 is continuously generated, the reflected light 440 having the same time zone as the totally-reflected light exists among the reflected light 440.

Referring to FIG. 5C, it can be seen that the interfering light generated by making the reflected light 440 having the same time zone as the totally-reflected light interfere with the totally-reflected light appears at the same time zone.

The point of time at which the totally-reflected light is generated varies whenever the light traveling distance 330 varies, and the point of time at which the interfering light is generated also varies accordingly. That is, the interfering light having various intensities is generated at the time zones at which the totally-reflected light corresponding to the light traveling distances 330 are generated.

In the aforementioned operation of the present apparatus, the light entering the light reflecting unit 210 and the light entering the optical probe 220 are emitted from the same light source unit 200. However, light emitted from different light source units 200 may respectively enter the light reflecting unit 210 and the optical probe 220. In addition, the light reflecting unit 210 may be replaced with a light irradiating unit (not shown). The light irradiating unit irradiates light to the optical device 230. It is possible to control the distance which the light irradiated by the light irradiating unit travels until it reaches the optical device 230.

Figure 6:
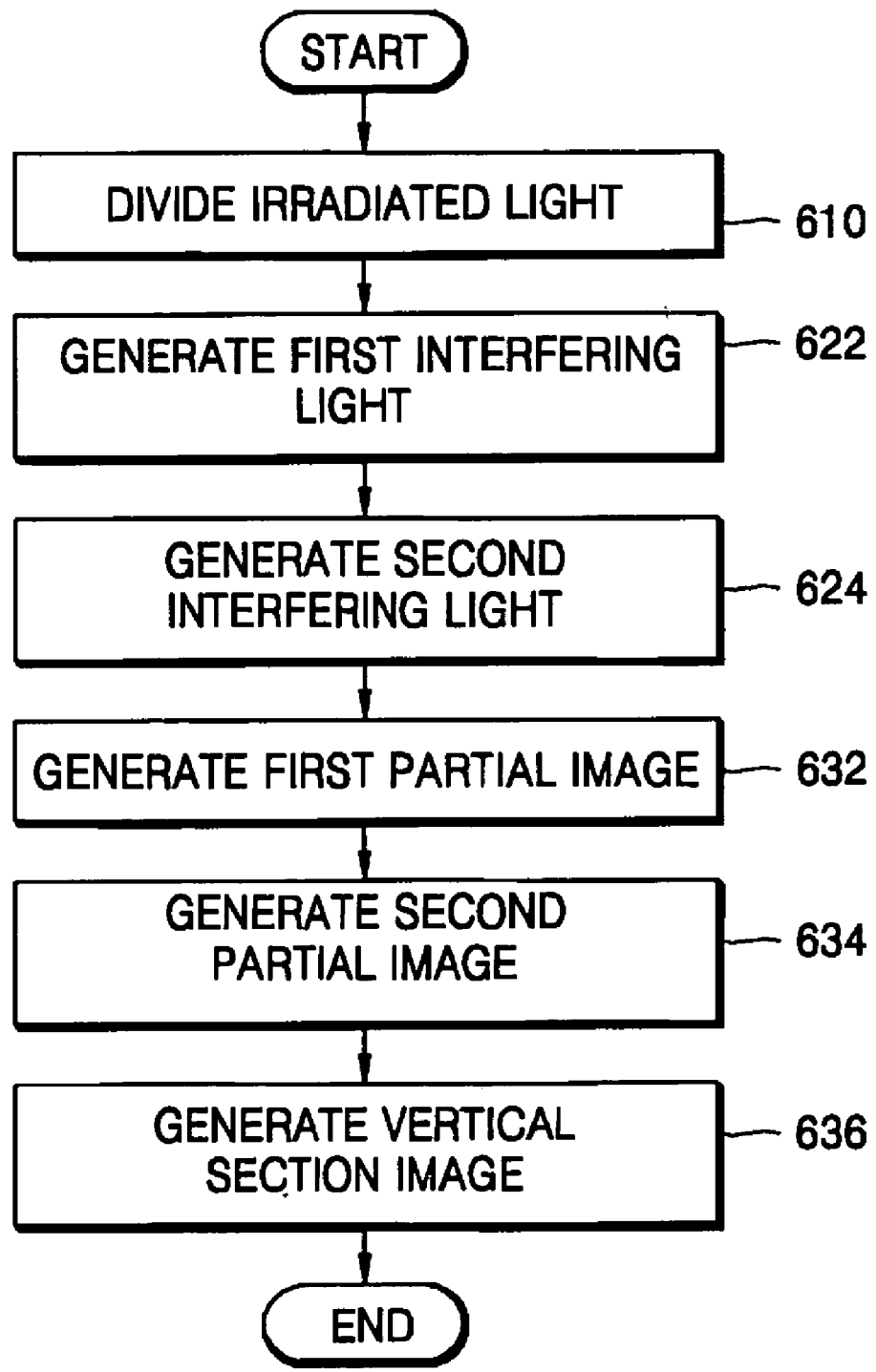
FIG. 6 is a flowchart illustrating a method of measuring the thickness of lingual fur and acquiring a vertical section image thereof according to an embodiment of the present invention.

FIG. 6 is a flowchart illustrating a method of measuring the thickness of lingual fur and acquiring a vertical section image thereof according to an embodiment of the present invention.

Referring to the figure, the optical device 230 of the present apparatus receives the light irradiated by the light source unit 200 and divides the light into a first part of the light and a second part of the light (operation 610).

The optical device 230 dividing the light from the light source unit 200 synthesizes first reflected light generated by totally reflecting the first part of the light, and second reflected light generated by irradiating the second part of the light to the tongue tissue 420, and generates first interfering light (operation 622).

When the distance that the first part of the light travels until it is totally reflected varies, the optical device 230 synthesizes third reflected light generated by totally reflecting the first part of the light and the second reflected light, and generates a second interfering light (operation 624).

The image generating unit 240 receives the first interfering light and generates a first partial image corresponding to the relative intensity of the first interfering light (operation 632). The image generating unit 240 receives the second interfering light generated whenever the optical distance varies, and generates one or more second partial images corresponding to the relative intensities of the second interfering lights (operation 634).

The image generating unit 240 synthesizes the first partial image and the one or more second partial images and generates a vertical section image of the lingual fur (operation 636).

As described above, using the method of measuring the thickness of the lingual fur and acquiring a vertical section image according to the present invention, and the apparatus to perform the method, it is possible to easily observe the vertical section image of the lingual fur and thus to more precisely examine the lingual fur.

In addition to the above-described embodiments, the method of the present invention can also be implemented by executing computer readable code/instructions in/on a medium, e.g., a computer readable medium. The medium can correspond to any medium/media permitting the storing and/or transmission of the computer readable code. The code/instructions may form a computer program.

The computer readable code/instructions can be recorded/transferred on a medium in a variety of ways, with examples of the medium including magnetic storage media (e.g., ROM, floppy disks, hard disks, etc.), optical recording media (e.g., CD-ROMs, or DVDs), and storage/transmission media such as carrier waves, as well as through the Internet, for example. The medium may also be a distributed network, so that the computer readable code/instructions is stored/transferred and executed in a distributed fashion. The computer readable code/instructions may be executed by one or more processors.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An apparatus to acquire a vertical section image of lingual fur, the apparatus comprising:
    a light irradiating unit having a light source to irradiate light, the light source being movable to the lingual fur and tongue tissue;
    an optical probe to receive the light irradiated from the light source and deliver the light to the lingual fur and the tongue tissue;
    an optical device to generate interfering light from the light irradiated from the light irradiating unit, the light reflected from the lingual fur, and the light reflected from the tongue tissue; and
    an image generating unit to generate a partial interfering light intensity-based image based on a relative intensity of the generated interfering light.

2. The apparatus according to claim 1, wherein the optical probe comprises an optical film provided at one end of the optical probe to be in close proximity with the tongue tissue.

3. The apparatus according to claim 1, wherein the light delivered by the optical probe is vertically irradiated to the tongue tissue.

4. The apparatus according to claim 1, further comprising a diagnosis unit to receive the image generated by the image generating unit, and to generate details of a prescription corresponding to the received image.

5. The apparatus according to claim 1, further comprising a user display unit to display the image generated by the image generating unit.

6. The apparatus according to claim 1, wherein the light irradiating unit, optical probe, optical device, and image generating unit are coupled together through optical cables.

7. The apparatus according to claim 1, wherein the light source has a wavelength of approximately 700 to 1300 nm and a bandwidth of approximately 10 to 100 nm.

8. An apparatus to acquire a vertical section image of lingual fur, the apparatus comprising:
    a light reflecting unit to receive light irradiated from a first predetermined light source and reflect the light;
    an optical probe to receive light irradiated from a second predetermined light source and deliver the light to the lingual fur and a tongue tissue;
    an optical device to generate interfering light from the light reflected by the light reflecting unit and the light reflected from the lingual fur and the light reflected from the tongue tissue; and
    an image generating unit to generate a partial interfering light intensity-based image based on a relative intensity of the generated interfering light.

9. The apparatus of claim 8, wherein the light reflecting unit comprises a lens to maintain a constant traveling direction of the light inside the light reflecting unit.

10. The apparatus according to claim 8, wherein the first predetermined light source applying light to the light reflecting unit and the second predetermined light source applying light to the optical probe comprise a single light source
    wherein the light reflecting unit reflects a first part of the light irradiated by the single light source;
    wherein the optical probe irradiates a second part of the light irradiated by the single light source to the tongue tissue; and
    wherein the optical device divides the light irradiated from the single light source into light irradiated to the light reflecting unit and light irradiated to the optical probe, and generates the interfering light from the light reflected by the light reflecting unit and the light reflected from the tongue tissue.

11. The apparatus according to claim 8, wherein the light reflecting unit comprises:
    a reflecting mirror to reflect the received light; and
    a driving motor to change a distance that the light irradiated to the reflecting mirror travels until reaching the reflecting mirror by moving the reflecting mirror.

12. The apparatus according to claim 8, wherein the optical probe comprises an optical film provided at one end of the optical probe to be in close proximity with the tongue tissue.

13. The apparatus according to claim 8, wherein the light reflecting unit totally reflects the received light.

14. The apparatus according to claim 8, wherein the light delivered by the optical probe is vertically irradiated to the tongue tissue.

15. The apparatus according to claim 11, wherein the image generating unit synthesizes partial images corresponding to positions of the moved reflecting mirror and generates the vertical section image.

16. The apparatus according to claim 8, further comprising a diagnosis unit to receive the image generated by the image generating unit, and to generate details of a prescription corresponding to the received image.

17. The apparatus according to claim 8, further comprising a user display unit to display the image generated by the image generating unit.

18. A method of acquiring a vertical section image of lingual fur, the method comprising:
   generating interfering light from irradiated light and light reflected from the lingual fur and a tongue tissue; and
   generating a partial interfering light intensity-based image based on a relative intensity of the generated interfering light.

19. The method according to claim 18, the method further comprising generating details of a prescription corresponding to the generated partial image.

20. The method according to claim 18, the method further comprising generating and displaying the vertical section image corresponding to one or more of the partial images.

21. A method of acquiring a vertical section image of lingual fur, the method comprising:
   dividing irradiated light into a first part and a second part;
   generating interfering light from reflected light of the first part of the light and reflected light from the lingual and a tongue tissue generated by irradiating the second part of the light to the lingual fur and to the tongue tissue; and
   generating a partial interfering intensity-based image based on a relative intensity of the generated interfering light.

22. The method according to claim 21, wherein the generation of the interfering light includes varying a distance that the first part of the light travels from a point at which the irradiated light is divided to a point at which the first part of the light is reflected; and
   wherein the generation of the partial image includes synthesizing a plurality of partial images corresponding to the varied distances that the first part of light travels, and generating the vertical section image.

23. The method according to claim 21, the method further comprising generating details of a prescription corresponding to the generated image.

24. The method according to claim 21, the method further comprising generating and displaying the vertical section image corresponding to one or more of the partial images.

25. The method according to claim 22, the method further comprising displaying the generated vertical section image.

26. At least one computer readable medium storing instructions that control at least one processor to perform a method of acquiring a vertical section image of lingual fur, the method comprising:
   generating interfering light from irradiated light and light reflected from the lingual fur and a tongue tissue; and
   generating a partial interfering light intensity-based image based on a relative intensity of the generated interfering light.

27. At least one computer readable medium storing instructions that control at least one processor to perform a method of acquiring a vertical section image of lingual fur, the method comprising:
   dividing irradiated light into a first part and a second part;
   generating interfering light from reflected light of the first part of the light and reflected light from the lingual fur and reflected light from a tongue tissue generated by irradiating the second part of the light to the lingual fur and the tongue tissue; and
   generating a partial interfering intensity-based image based on a relative intensity of the generated interfering light.

28. A method of acquiring a vertical section image of lingual fur, the method comprising:
   generating partial interfering intensity-based images from light reflected from the lingual fur and from tongue tissue; and
   synthesizing the partial interfering intensity-based images to generate the vertical section image.

29. The method of claim 28, wherein the generating the partial images comprises:
   irradiating and reflecting a first light;
   irradiating a second light to, and reflecting the second light from, the tongue tissue; and
   generating interfering light from the reflected first and second light;
   wherein the partial images are generated from the interfering light.

30. The method of claim 29, wherein the partial images correspond to a relative intensity of the generated interfering light.

31. The method of claim 29, wherein the first and second lights share a common source.

* * * * *

UNITED STATES PATENT AND TRADEMARK OFFICE
CERTIFICATE OF CORRECTION

PATENT NO. : 7,518,734 B2 Page 1 of 1
APPLICATION NO. : 11/272141
DATED : April 14, 2009
INVENTOR(S) : In-duk Hwang et al.

It is certified that error appears in the above-identified patent and that said Letters Patent is hereby corrected as shown below:

Column 9, Line 18, change "lingual and" to --lingual fur and--.

Signed and Sealed this

Twenty-third Day of June, 2009

JOHN DOLL
*Acting Director of the United States Patent and Trademark Office*